(12) United States Patent
Takeuchi et al.

(10) Patent No.: US 8,703,108 B2
(45) Date of Patent: Apr. 22, 2014

(54) CLEANSING COMPOSITION

(71) Applicant: Kao Corporation, Tokyo (JP)

(72) Inventors: Hiroki Takeuchi, Bunkyo-ku (JP);
Masahiro Miyaki, Higashimurayama (JP); Naoko Yamamoto, Taito-ku (JP); Natsuko Toshida, Wakayama (JP); Jurgen Benade, Rees (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/760,096

(22) Filed: Feb. 6, 2013

(65) Prior Publication Data

US 2013/0149276 A1    Jun. 13, 2013

Related U.S. Application Data

(63) Continuation of application No. PCT/JP2011/070043, filed on Sep. 2, 2011.

(30) Foreign Application Priority Data

Sep. 3, 2010    (JP) .................. 2010-197494

(51) Int. Cl.
| | |
|---|---|
| *A61K 8/00* | (2006.01) |
| *A61K 8/18* | (2006.01) |
| *A61K 8/81* | (2006.01) |
| *A61K 8/35* | (2006.01) |
| *A61Q 5/06* | (2006.01) |
| *A61Q 5/12* | (2006.01) |
| *C07C 69/74* | (2006.01) |
| *C07C 229/00* | (2006.01) |
| *C07C 61/08* | (2006.01) |

(52) U.S. Cl.
USPC ............... 424/70.1; 424/70.16; 424/70.22; 424/70.27; 424/70.28; 424/70.31; 560/1; 560/129; 560/155; 562/400; 562/512

(58) Field of Classification Search
USPC ............ 424/70.1, 70.16, 70.22, 70.27, 70.28, 424/70.31; 560/1, 129, 155; 562/400, 512
See application file for complete search history.

(56) References Cited

U.S. PATENT DOCUMENTS

| | | |
|---|---|---|
| 2007/1006650 | 3/2007 | Yang et al. |
| 2007/0269397 A1* | 11/2007 | Terada ...................... 424/70.12 |
| 2008/0261845 A1 | 10/2008 | Yamamoto et al. |

FOREIGN PATENT DOCUMENTS

| | | | |
|---|---|---|---|
| CN | 1148377 A | | 4/1997 |
| JP | 61-21199 | * | 1/1986 |

(Continued)

OTHER PUBLICATIONS

Japanese Office Action issued Aug. 28, 2012, in Patent Application No. 2011-191761.

(Continued)

*Primary Examiner* — Jane C Oswecki
(74) *Attorney, Agent, or Firm* — Oblon, Spivak, McClelland, Maier & Neustadt, L.L.P.

(57) ABSTRACT

Cleansing compositions include a mixture of alkyl ether carboxylic acids and/or salts thereof, each having a structure according to formula (1):

$$R^1-O-(CH_2CH_2O)_n-CH_2-COOM \qquad (1)$$

where $R^1$ is an alkyl group having 4 to 22 carbon atoms, n is a number of from 0 to 20, and M is a hydrogen atom, alkali metal, alkaline earth metal, ammonium, or organic ammonium. The mixture includes alkyl ether carboxylic acids and/or salts having at least two different alkyl groups $R^1$, an average carbon number of alkyl groups $R^1$ of alkyl ether carboxylic acids and/or salts in the mixture is from 10.8 to 12.5, the mixture includes alkyl ether carboxylic acids and/or salts in which n=0 in an amount of from 8 to 27% by weight based on a total weight of the mixture, the mixture includes alkyl ether carboxylic acids and/or salts in which n=1 and alkyl ether carboxylic acids and/or salts in which n=2 in an amount of from 28 to 38% by weight based on the total weight of the mixture, and the mixture includes alkyl ether carboxylic acids and/or salts in which n≤6 in an amount of at least 10% by weight based on the total weight of the mixture.

18 Claims, 1 Drawing Sheet

Photograph 1

Photograph 2

(56) References Cited

FOREIGN PATENT DOCUMENTS

| | | | |
|---|---|---|---|
| JP | 2-175799 | * | 7/1990 |
| JP | 7-48222 | | 2/1995 |
| JP | 11-508268 | | 7/1999 |
| JP | 2001-207189 | | 7/2001 |
| JP | 2003-119500 | | 4/2003 |
| JP | 2006-192375 | | 7/2006 |
| JP | 2007-112984 | | 5/2007 |
| JP | 2008-285479 | | 11/2008 |
| WO | 95/32174 A1 | | 11/1995 |
| WO | WO 97/01328 | | 1/1997 |

OTHER PUBLICATIONS

"Pamphlet about Perfumery and cosmetics, pharmaceutical products raw materials of KAO", KAO Corporation, May 2007, 2 pages (with unedited computer-generated English translation).
English translation of the International Preliminary Report on Patentability and Written Opinion issued Apr. 18, 2013, in PCT/JP2011/070043, filed Sep. 2, 2011.
International Search Report mailed Nov. 22, 2011, in PCT/JP2011/070043 filed Sep. 2, 2011.

* cited by examiner

Photograph 1
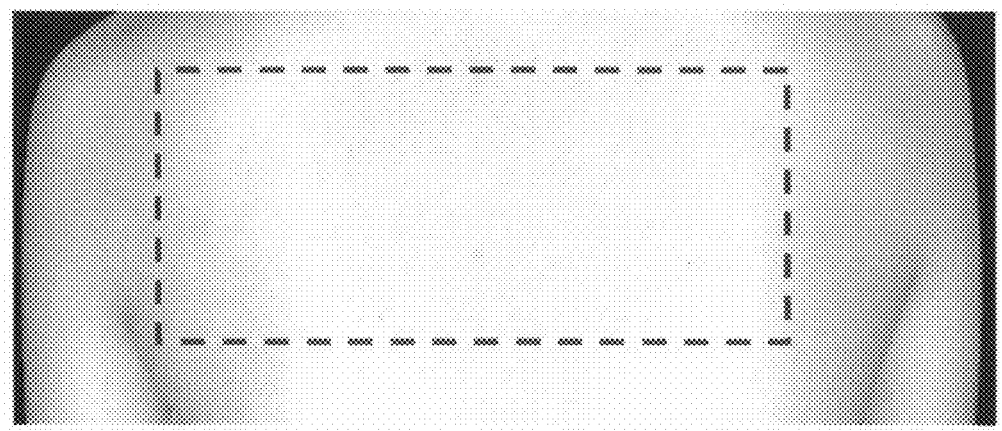
Photograph 2
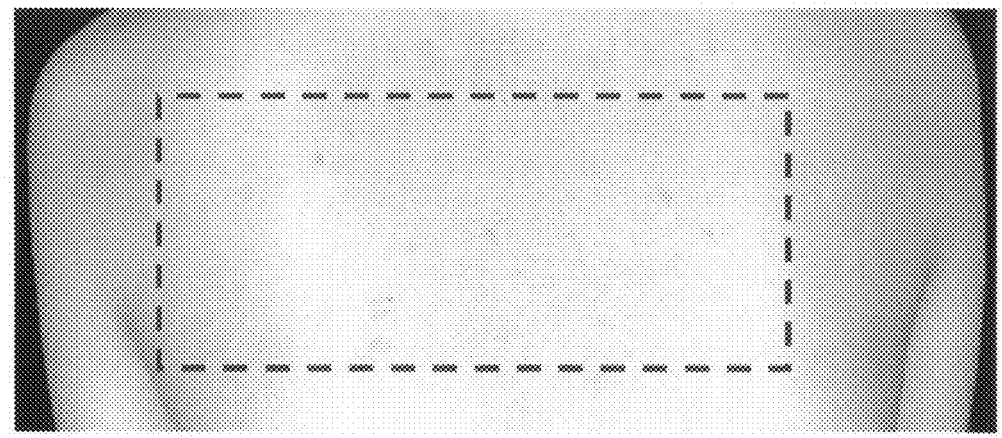

CLEANSING COMPOSITION

CROSS REFERENCES TO RELATED APPLICATIONS

This application is a continuation of International Patent Application No. PCT/JP2011/070043, filed on Sep. 2, 2011, and claims priority to Japanese Patent Application No. 2010-197494, filed on Sep. 3, 2010.

CROSS REFERENCE TO RELATED APPLICATIONS

This application is a continuation of International Application No. PCT/JP2011/070043, filed Sep. 2, 2011, the disclosure of which is incorporated herein by reference in its entirety. This application claims priority to Japanese Patent Application No. 2010-197494, filed Sep. 3, 2010, the disclosure of which is incorporated herein by reference in its entirety.

BACKGROUND

The present invention relates to a cleansing composition.

Conventionally, as skin cleansing agents, anionic surfactants such as alkyl sulfate, polyoxyethylene alkyl sulfate, and higher fatty acid salts have been used. However, use of such surfactants presents problems such a slimy feeling during rinsing and a tight feeling after use, as in JP-A-2007-112984 and JP-A-H11-508268. Also, it has occasionally been observed that when these skin cleansing agents are applied by hand, pimples appear in areas that are difficult to reach by hand, such as the back. One possible reason for the foregoing difficulties is that sebum cannot be completely washed off and thus accumulates on the skin. In view of the above, a cleansing agent which is less irritating to the skin and has a good ability to wash off sebum (i.e., sebum cleansing properties) is desired.

Although alkyl ether carboxylic acid-based surfactants are known to be gentle to the skin, they have poor foaming properties. Thus, the use of these surfactants in combination with other surfactants such as alkyl ether sulfates has been considered. However, when such combinations of surfactants have been used, a feeling that rinsing has concluded, i.e., a feeling of friction during rinsing, is lessened. In view of this difficulty, various attempts to improve the rinsing properties of such combinations of surfactants have been made, as, for example, in JP-A-2008-285479.

Also, attempts have been made to prepare cleansing compositions containing an ether carboxylic acid-based surfactant having improved foamability. Such cleansing compositions have included ether carboxylic acid-based surfactants with narrow molecular weight distribution, as in JP-A-S61-21199 and JP-A-2001-207189. Further, a cleansing composition containing an ether carboxylic acid-based surfactant having a specific distribution of added moles of ethylene oxide has been proposed, as in JP-A-H02-175799.

Notwithstanding the foregoing efforts, known cleansing compositions remain unsatisfactory with respect to the amount of time required to obtain a feeling that rinsing has concluded, and have insufficient sebum cleansing properties.

SUMMARY

In various exemplary embodiments, cleansing compositions according to the present invention include a mixture of alkyl ether carboxylic acids and/or salts thereof, each having a structure according to formula (1):

$$R^1-O-(CH_2CH_2O)_n-CH_2-COOM \quad (1)$$

where $R^1$ is an alkyl group having 4 to 22 carbon atoms, n is a number of from 0 to 20, and M is a hydrogen atom, alkali metal, alkaline earth metal, ammonium, or organic ammonium. In embodiments, the mixture includes alkyl ether carboxylic acids and/or salts having at least two different alkyl groups $R^1$. In embodiments, an average carbon number of alkyl groups $R^1$ of alkyl ether carboxylic acids and/or salts in the mixture is from 10.8 to 12.5. In embodiments, the mixture includes alkyl ether carboxylic acids and/or salts in which n=0 in an amount of from 8 to 27% by weight based on a total weight of the mixture. In embodiments, the mixture includes alkyl ether carboxylic acids and/or salts in which n=1 and alkyl ether carboxylic acids and/or salts in which n=2 in an amount of from 28 to 38% by weight based on the total weight of the mixture. In embodiments, the mixture includes alkyl ether carboxylic acids and/or salts in which n≤6 in an amount of at least 10% by weight based on the total weight of the mixture.

In various exemplary embodiments, the present invention includes a skin cleansing method, in which cleansing compositions as described herein are applied to an area of skin, the skin is washed, and the skin is rinsed.

Exemplary cleansing compositions according to the present invention are excellent in foaming performance, having good foaming properties, volume of foam, and foam qualities. Exemplary cleansing compositions according to the present invention have favorable rinsing properties. Exemplary cleansing compositions according to the present invention have good sebum cleansing properties, and thus can alleviate pimples on the back and patchy redness of the skin. Furthermore, after washing, exemplary cleansing compositions according to the present invention impart a smooth feeling to the skin even under conditions of high temperature and high humidity.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 1 includes a photograph of a back that has been washed with the cleansing agent of Example 19 for three weeks (Photograph 1) and a photograph of a back that has been washed with the cleansing agent of Comparative Example 16 for three weeks (Photograph 2).

DETAILED DESCRIPTION OF EXEMPLARY EMBODIMENTS

Other features of the invention will become apparent in the course of the following descriptions of exemplary embodiments which are given for illustration of the invention and are not intended to be limiting thereof.

The present invention relates to cleansing compositions which have excellent foaming and rinsing properties and excellent sebum cleansing properties.

The present inventors have found that cleansing agents having not only excellent foaming performance, favorable rinsing properties, and a good feel, but also excellent sebum cleansing properties, can be obtained by using a mixture of alkyl ether carboxylates having a specific distribution. Such mixtures may be obtained by any suitable means such as described, for example, in the examples below.

In various exemplary embodiments, cleansing compositions according to the present invention include a mixture of alkyl ether carboxylic acids or salts thereof according to formula (1).

$$R^1-O-(CH_2CH_2O)_n-CH_2-COOM \quad (1)$$

In embodiments, $R^1$ is an alkyl group having 4 to 22 carbon atoms, preferably an alkyl group having 10 to 16 carbon atoms, more preferably an alkyl group having 12 to 14 carbon atoms. Also, although the alkyl chain of $R^1$ may be either linear or branched, from the viewpoint of foaming properties, a linear alkyl group is preferred. Also, in embodiments, the mixture includes compounds having two or more different alkyl groups $R^1$ and has an average carbon number of from 10.8 to 12.5, preferably from 12.1 to 12.4. It is preferable that the average carbon number be within the above range since excellent foaming properties, foam qualities, and stability at low temperature are obtained.

In embodiments, the mixture includes compounds having two or more different alkyl groups $R^1$ and, and a content of a compound having an alkyl chain length which is contained in the highest content is preferably 55% by weight or more and less than 97% by weight, more preferably from 60 to 95% by weight, and even more preferably from 70 to 95% by weight since excellent volume of foam and foam qualities are obtained.

In embodiments, in formula (1), n represents a number of from 0 to 20, preferably from 0 to 12. In embodiments, the mixture of alkyl ether carboxylic acids or salts thereof includes compounds having different values for n, and an average value of n for the alkyl ether carboxylic acids or salts thereof in the mixture is preferably from 1.5 to 3.5, more preferably from 2.7 to 3.4, and even more preferably from 2.8 to 3.1. Selecting such preferred average values of n results in favorable foaming properties. In embodiments, n represents the number of moles of ethylene oxide added during preparation of the mixture of alkyl ether carboxylic acids or salts thereof.

In embodiments, the mixture includes compounds in which n=0 in an amount of preferably from 8 to 27% by weight, more preferably from 12 to 27% by weight, even more preferably from 13 to 27% by weight. In particularly preferred embodiments, the mixture includes compounds in which n=0 in an amount of 14 to 18% by weight or 14 to 17% by weight. When the content of compounds in which n=0 is within the above range, the resulting cleansing composition will have not only excellent detergency but also high foaming properties, a fresh feeling during rinsing, and an improved feeling of friction, and further, the cleansing composition can give a smooth feel even to skin that tends to become sticky under high humidity.

Also, in embodiments, the mixture includes compounds in which n=1 and n=2 in a total amount of from 28 to 38% by weight, preferably from 31 to 38% by weight. It is preferable that the total content of compounds in which n=1 and 2 be within the above range since excellent volume of foam and foam qualities are obtained.

Further, in embodiments, the mixture includes compounds in which n≤6 in an amount of preferably 10% by weight or more, more preferably from 10 to 25% by weight, even more preferably from 12 to 25% by weight. In further embodiments, the mixture includes compounds in which n≤6 in an amount of 14 to 25% by weight, more preferably from 14 to 22% by weight, and even more preferably from 14 to 18% by weight. When the content of compounds in which n≤6 is within the above ranges, the resulting product will have an improved stability at low temperature when used as a cleansing agent.

Also, examples of M include a hydrogen atom; an alkali metal such as sodium and potassium; an alkaline earth metal such as calcium and magnesium; ammonium; an alkanolamine-derived ammonium such as monoethanolamine, diethanolamine, and triethanolamine. Among them, an alkali metal is preferred in terms of foaming properties, stability at low temperature, and absence of coloration over time.

In embodiments of the cleansing composition according to the present invention, the mixture of compounds according to formula (1) includes alkyl ether carboxylic acids and/or salts in a weight ratio of $(W_0):(W_1):(W_2):(W_3):(W_4)$ of (1):(0.99 to 3.50):(0.89 to 3.00):(0.76 to 3.00):(0.63 to 1.52), where $W_0$ is a total weight of alkyl ether carboxylic acids and/or salts in the mixture in which n=0, $W_1$ is a total weight of alkyl ether carboxylic acids and/or salts in the mixture in which n=1, $W_2$ is a total weight of alkyl ether carboxylic acids and/or salts in the mixture in which n=2, $W_3$ is a total weight of alkyl ether carboxylic acids and/or salts in the mixture in which n=3, and $W_4$ is a total weight of alkyl ether carboxylic acids and/or salts in the mixture in which n=4. When the foregoing ratio is employed, good foaming properties, detergency, and a feeling of friction during rinsing can be achieved simultaneously.

In embodiments of the cleansing composition according to the present invention, the mixture includes alkyl ether carboxylic acids and/or salts in which n=0 in an amount of from 8 to less than 12% by weight, and preferably from 9 to less than 12% by weight based, on a total weight of the mixture, and the mixture includes alkyl ether carboxylic acids and/or salts in a weight ratio of $(W_0):(W_1):(W_2):(W_3):(W_4)$ of (1): (1.53 to 1.87):(1.59 to 2.25):(1.33 to 2.16):(1.00 to 1.52). Alternatively, the mixture includes alkyl ether carboxylic acids and/or salts in which n=0 in an amount of from 12 to 17% by weight based on a total weight of the mixture, and the mixture includes alkyl ether carboxylic acids and/or salts in a weight ratio of $(W_0):(W_1):(W_2):(W_3):(W_4)$ of (1):(0.99 to 1.34):(0.89 to 1.40):(0.76 to 1.23):(0.63 to 0.99). Employing the foregoing compositions provides even more excellent foaming properties, detergency, and feeling of friction during.

In embodiments of the cleansing composition according to the present invention, the mixture includes alkyl ether carboxylic acids and/or salts in which n=0 in an amount of from 8 to 11.8% by weight by weight based on a total weight of the mixture, and the mixture includes alkyl ether carboxylic acids and/or salts in a weight ratio of $(W_0):(W_1):(W_2):(W_3):(W_4)$ of (1):(1.58 to 1.84):(1.72 to 2.17):(1.49 to 2.00):(1.00 to 1.52). The foregoing composition provides excellent detergency is achieved and a fresh feeling after rinsing. In further embodiments, the mixture includes alkyl ether carboxylic acids and/or salts in which n=0 in an amount of from 13 to 17% by weight based on a total weight of the mixture, and the mixture includes alkyl ether carboxylic acids and/or salts in a weight ratio of $(W_0):(W_1):(W_2):(W_3):(W_4)$ of (1):(1.00 to 1.31):(0.93 to 1.34):(0.79 to 1.18):(0.63 to 0.99). This composition provides excellent detergency and a feeling of friction during rinsing.

In embodiments of the cleansing composition according to the present invention, the mixture includes alkyl ether carboxylic acids and/or salts in which n=0 in an amount of from 13 to 16% by weight based on a total weight of the mixture, and the mixture includes alkyl ether carboxylic acids and/or salts in a weight ratio of $(W_0):(W_1):(W_2)\ (W_3):(W_4)$ of (1): (1.00 to 1.25):(1.10 to 1.30):(0.85 to 1.10):(0.65 to 0.90), and preferably (1):(1.20 to 1.21):(1.17 to 1.24):(0.94 to 1.04):

(0.69 to 0.83). The foregoing composition simultaneously provides good foaming properties, foam qualities, detergency, and a feeling of friction during rinsing.

In embodiments of the cleansing composition according to the present invention, in the mixture of alkyl ether carboxylic acids or salts thereof represented by the formula (1), $R^1$ includes two or more alkyl groups and has an average carbon number of 10.8 to 12.5, compounds in which n=0 are present in an amount of from 13 to 27% by weight, and compounds in which n≤6 are present in an amount of 10% by weight or more.

In embodiments of the cleansing composition according to the present invention, in the mixture of alkyl ether carboxylic acids and/or salts thereof according to formula (1), $R^1$ is an alkyl group having 4 to 22 carbon atoms, n is a number of from 0 to 20, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 10.8 to 12.5. The mixture includes alkyl ether carboxylic acids and/or salts having alkyl groups $R^1$ having a highest carbon number in an amount of from 55 to less than 97% by weight based on the total weight of the mixture. An average value of n of alkyl ether carboxylic acids and/or salts in the mixture is from 2.7 to 3.4, and preferably 2.8 to 3.1. The mixture includes alkyl ether carboxylic acids and/or salts in which n=0 in an amount of from 12 to 27% by weight, and preferably 13 to 27% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 10 to 25% by weight based on the total weight of the mixture. A cleansing composition including a mixture of alkyl ether carboxylic acids or salts thereof having the foregoing composition can achieve accelerated foaming and creamy foam qualities.

In embodiments of the cleansing composition according to the present invention, in the mixture of alkyl ether carboxylic acids and/or salts thereof according to formula (1), $R^1$ is an alkyl group having 10 to 16, and preferably 12 to 14 carbon atoms, n is a number of from 0 to 20, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts having alkyl groups $R^1$ having a highest carbon number in an amount of from 55 to less than 97% by weight based on the total weight of the mixture. An average value of n of alkyl ether carboxylic acids and/or salts in the mixture is from 1.5 to 3.5. The mixture includes alkyl ether carboxylic acids and/or salts in which n=0 in an amount of from 12 to 27% by weight, and preferably 13 to 27% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 10 to 25% by weight based on the total weight of the mixture. A cleansing composition including a mixture of alkyl ether carboxylic acids or salts thereof having the foregoing composition can achieve accelerated foaming and creamy foam qualities.

In embodiments of the cleansing composition according to the present invention, in the mixture of alkyl ether carboxylic acids and/or salts thereof according to formula (1), $R^1$ is an alkyl group having 4 to 22 carbon atoms, n is a number of from 0 to 20, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 10.8 to 12.5. The mixture includes alkyl ether carboxylic acids and/or salts having alkyl groups $R^1$ having a highest carbon number in an amount of from 55 to less than 97% by weight based on the total weight of the mixture. An average value of n of alkyl ether carboxylic acids and/or salts in the mixture is from 1.5 to 3.5. The mixture includes alkyl ether carboxylic acids and/or salts in which n=0 in an amount of from 14 to 18% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 10 to 25% by weight based on the total weight of the mixture. A cleansing composition including a mixture of alkyl ether carboxylic acids or salts thereof having the foregoing composition can strengthen a stopping feeling during rinsing and suppress a sticky feeling under high temperature and high humidity.

In embodiments of the cleansing composition according to the present invention, in the mixture of alkyl ether carboxylic acids and/or salts thereof according to formula (1), $R^1$ is an alkyl group having 4 to 22 carbon atoms, n is a number of from 0 to 20, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 10.8 to 12.5. The mixture includes alkyl ether carboxylic acids and/or salts having alkyl groups $R^1$ having a highest carbon number in an amount of from 55 to less than 97% by weight based on the total weight of the mixture. An average value of n of alkyl ether carboxylic acids and/or salts in the mixture is from 1.5 to 3.5. The mixture includes alkyl ether carboxylic acids and/or salts in which n=0 in an amount of from 14 to 18% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 14 to 25% by weight, and preferably 14 to 25% by weight, based on the total weight of the mixture. A cleansing composition including a mixture of alkyl ether carboxylic acids or salts thereof having the foregoing composition can have improved stability at low temperature when prepared as an aqueous cleansing agent.

In embodiments of the cleansing composition according to the present invention, in the mixture of alkyl ether carboxylic acids and/or salts thereof according to formula (1), $R^1$ is an alkyl group having 10 to 16 carbon atoms, n is a number of from 0 to 20, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts having alkyl groups $R^1$ having a highest carbon number in an amount of from 60 to 95% by weight based on the total weight of the mixture. An average value of n of alkyl ether carboxylic acids and/or salts in the mixture is from 2.7 to 3.4. The mixture includes alkyl ether carboxylic acids and/or salts in which n=0 in an amount of from 14 to 18% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 14 to 25% by weight based on the total weight of the mixture. A cleansing composition including a mixture of alkyl ether carboxylic acids or salts thereof having the foregoing composition can have improved foaming properties and volume of foam, while avoiding problems such as stability at low temperature when prepared as an aqueous cleansing agent.

In embodiments of the cleansing composition according to the present invention, in the mixture of alkyl ether carboxylic acids and/or salts thereof according to formula (1), $R^1$ is an alkyl group having 12 to 14 carbon atoms, n is a number of from 0 to 12, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts having alkyl groups $R^1$ having a highest carbon number in an amount of from 70 to 95% by weight based on the total weight of the mixture. An average value of n of alkyl ether carboxylic acids and/or salts in the mixture is from 2.8 to 3.1. The mixture includes alkyl ether carboxylic acids and/or salts in which n=0 in an amount of from 14 to 18% by weight, based on a total weight of the mixture. The mixture includes alkyl ether carboxylic acids and/or salts in which n=1 and alkyl ether carboxylic acids and/or salts in which n=2 in a total amount of from 28 to 38% by weight based on the total weight of the mixture. The mixture includes alkyl ether carboxylic acids and/or salts in which n≤6 in an amount of from 14 to 22% by weight based on the total weight of the mixture. A cleansing composition including a mixture of alkyl ether carboxylic acids or salts thereof having the foregoing composition can have improved foaming properties, volume of foam, and foam qualities, while avoiding problems such as stability at low temperature when prepared as an aqueous cleansing agent.

In embodiments of the cleansing composition according to the present invention, in the mixture of alkyl ether carboxylic acids and/or salts thereof according to formula (1), $R^1$ is an alkyl group having 12 to 14 carbon atoms, n is a number of from 0 to 12, and M is a hydrogen atom, sodium, potassium, or ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts having alkyl groups $R^1$ having a highest carbon number in an amount of from 70 to 95% by weight based on the total weight of the mixture. An average value of n of alkyl ether carboxylic acids and/or salts in the mixture is from 2.8 to 3.1. The mixture includes alkyl ether carboxylic acids and/or salts in which n=0 in an amount of from 8 to less than 12% by weight, based on a total weight of the mixture. The mixture includes alkyl ether carboxylic acids and/or salts in which n=1 and alkyl ether carboxylic acids and/or salts in which n=2 in a total amount of from 31 to 38% by weight based on the total weight of the mixture. The mixture includes alkyl ether carboxylic acids and/or salts in which n≤6 in an amount of from 12 to 25% by weight based on the total weight of the mixture. A cleansing composition including a mixture of alkyl ether carboxylic acids or salts thereof having the foregoing composition can have improved foaming properties, volume of foam, and foam qualities, while avoiding problems such as stability at low temperature when prepared as an aqueous cleansing agent.

The distribution of the alkyl chain length of $R^1$, the average alkyl chain length of $R^1$, the amount of a component in which n=0, the total amount of a component in which n=1 and a component in which n=2, the total amount of components in which n≤6, the average number of added moles n, and a weight ratio of the components in which n=0, 1, 2, 3, and 4 in the mixtures of compounds according to formula (1) may be determined by gas chromatographic analysis as described below.

[Distribution of the Alkyl Chain Length of $R^1$]

From the peak areas obtained by gas chromatography, a peak area of each alkyl chain length corresponding to n=0 mole is obtained, and setting the sum of the peak areas thus obtained at 100, the percentage of the distribution of each alkyl chain length is calculated. A similar calculation is carried out also as to n=1 to 3 moles, and the percentage values of the distribution of each alkyl chain length corresponding to n=0 to 3 moles are averaged out, whereby the distribution of the alkyl chain length of $R^1$ is obtained (from this, the alkyl group component contained in the largest amount in the composition of $R^1$ can be specified).

[Average Alkyl Chain Length of $R^1$]

From the distribution of the alkyl chain length of $R^1$ obtained as above, the proportion of each component is obtained, which is multiplied by the number of carbon atoms of the corresponding alkyl chain length, and the resulting values are summed. The value thus obtained is used as an average alkyl chain length.

[Amount of a component in which n=0, total amount of a component in which n=1 and a component in which n=2, and total amount of components in which n≤6]

In the composition of $R^1$, the alkyl chain length which is contained in the highest content is specified, and the peak areas of the component having the alkyl chain length of the highest content corresponding to n=0 to 10 are added up by gas chromatography. By setting the total amount thus obtained at 100%, the amount of a component in which n=0, the total amount of a component in which n=1 and a component in which n=2, and the total amount of components in which n≤6 are calculated.

[Average number of added moles n]

In the composition of R', the alkyl chain length of the highest content is specified, and the peak areas of the component having the alkyl chain length of the highest content corresponding to n=0 to 10 are added up by gas chromatography (the amount of a component in which n is 11 or more is so small that it is excluded from the calculation). By setting the total amount thus obtained at 1, each proportion of n=0 to 10 is obtained. The resulting proportion is multiplied by each number of added moles, and the sum of the resulting values is used as the average number of added moles n.

[Weight ratio of the components in which n=0, 1, 2, 3, and 4]

As to the ratio of each of the components having different numbers of moles of EO added, the distribution of the alkyl chain length of $R^1$ is obtained from the peak area obtained by gas chromatography by the method described above, and the component having the alkyl chain length of the highest content in the composition of $R^1$ is specified, and the ratio of each of the components having different numbers of moles of EO added is specified by the area ratio of n=0, n=1, n=2, n=3, and n=4 of the component having the alkyl chain length of the highest content.

In various exemplary embodiments of the cleansing composition according to the present invention, mixtures of alkyl ether carboxylic acids or salts thereof according to formula (1) may have the aforementioned compositions, and may be included in an amount of preferably from 0.5 to 20% by weight, more preferably from 1 to 15% by weight of the total composition to achieve excellent detergency, sebum cleansing properties, and smooth skin feel.

In embodiments, the cleansing composition according to the present invention may further include water as a solvent. Water may be included in an amount of preferably from 3 to 99% by weight, more preferably from 10 to 95% by weight of the total composition, and is added as balance of the mixture of alkyl ether carboxylic acids or salts thereof according to formula (1) and other components of the cleansing composition.

A preferred cleansing composition according to the present invention includes a mixture of alkyl ether carboxylic acids and/or salts thereof, each having a structure according to formula (1):

in which $R^1$ is an alkyl group having 4 to 22 carbon atoms, n is a number of from 0 to 20, and M is a hydrogen atom, alkali metal, alkaline earth metal, ammonium, or organic ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts in which n=0 in an amount of from 8 to less than 12% by weight, preferably from 9.8 to 11.8% by weight, based on a total weight of the mixture. The mixture includes alkyl ether carboxylic acids and/or salts in a weight ratio of $(W_0):(W_1):(W_2):(W_3):(W_4)$ of (1):(1.53 to 1.87):(1.59 to 2.25):(1.33 to 2.16):(1.00 to 1.52), and preferably (1):(1.58 to 1.84):(1.72 to 2.17):(1.49 to 2.00):(1.14 to 1.52). The mixture includes alkyl ether carboxylic acids and/or salts in which n=1 and alkyl ether carboxylic acids and/or salts in which n=2 in a total amount of from 31 to 38% by weight based on the total weight of the mixture. The mixture includes alkyl ether carboxylic acids and/or salts in which n≤6 in an amount of from 14 to 18% by weight based on the total weight of the mixture.

A further preferred cleansing composition according to the present invention includes a mixture of alkyl ether carboxylic acids and/or salts thereof, each having a structure according to formula (1):

in which $R^1$ is an alkyl group having 4 to 22 carbon atoms, n is a number of from 0 to 20, and M is a hydrogen atom, alkali metal, alkaline earth metal, ammonium, or organic ammonium. The mixture includes alkyl ether carboxylic acids and/or salts having at least two different alkyl groups $R^1$, and an average carbon number of alkyl groups $R^1$ of alkyl ether carboxylic acids and/or salts in the mixture is from 12.1 to 12.4. The mixture includes alkyl ether carboxylic acids and/or salts in which n=0 in an amount of from 12 to less than 17% by weight, preferably from 13 to 16% by weight, based on a total weight of the mixture. The mixture includes alkyl ether carboxylic acids and/or salts in a weight ratio of $(W_0):(W_1):(W_2):(W_3):(W_4)$ of (1):(1.00 to 1.25):(1.10 to 2.30):(0.85 to 1.10):(0.65 to 0.90), and preferably (1):(1.20 to 1.21):(1.17 to 1.24):(0.94 to 1.04):(0.69 to 0.83). The mixture includes alkyl ether carboxylic acids and/or salts in which n=1 and alkyl ether carboxylic acids and/or salts in which n=2 in a total amount of from 31 to 38% by weight based on the total weight of the mixture. The mixture includes alkyl ether carboxylic acids and/or salts in which n≤6 in an amount of from 14 to 18% by weight based on the total weight of the mixture.

In various exemplary embodiments, the cleansing composition according to the present invention may further include components used in ordinary cleansing agents such as surfactants other than those represented by formula (1), humectants, oil components, disinfecting agents, anti-inflammatory agents, preservatives, chelating agents, thickening agents, pearlescent agents, fragrances, cooling agents, dyes, ultraviolet absorbers, antioxidants, and plant extracts.

In various exemplary embodiments, the cleansing composition according to the present invention is produced by mixing the blending components by a routine method. The cleansing composition thus obtained may be either liquid or solid; however, when it is liquid, the viscosity at 25° C. as measured by a B-type viscometer (manufactured by Tokyo Keiki Inc.) is preferably from 200 to 80000 mPa·s. The viscosity can be adjusted by appropriately selecting the blending components.

In various exemplary embodiments, the cleansing composition according to the present invention has a pH preferably from 3 to 12, and more preferably from 5 to 10.5. The pH may be measured after diluting the cleansing composition 20-fold with ion exchange water at 25° C.

In various exemplary embodiments, the cleansing composition according to the present invention may be prepared as, for example, a face wash, a body soap, a hand soap, and a hair cleansing agent. Among them, it is suitable as a skin cleansing composition such as a face wash and a body soap.

The present invention is also directed to a skin cleansing method using a cleansing composition as described herein. In embodiments, the skin cleansing method according to the present invention includes applying an adequate amount of a cleansing composition to the body, for example, the body's skin areas such as face, hands, feet, and torso, lathering up and washing, and then rinsing off using warm water from a shower and the like. It is also possible to apply an adequate amount of the cleansing composition to a washing aid such as a towel, a sponge, and a brush, and then lather up and wash.

(Measurement Method)

The distribution of the moles of EO added and the ratio of each component of alkyl ether carboxylic acids employed in cleansing compositions according to the present invention may be measured by gas chromatography (GC). Exemplary techniques for carrying out the measurement include Analytical Method 1 and Analytical Method 2 discussed below. Although the methods produce equivalent results, measurement is preferably conducted by Analytical Method 2 because when a product is analyzed, the analysis is less likely to be affected by other components.

(1) Analytical Method 1

(GC Measurement Conditions)

GC instrument: the product of Agilent Technologies, 6850 series II

Column: the product of Agilent Technologies, HP-ULTRA1 (25 m)

Detector: FID

Carrier: helium gas, 1 mL/min

Conditions of temperature rise: temperature is raised at a rate of 10° C./min from 100° C. to 300° C., and thereafter, maintained at 300° C. for 120 minutes.

(Method of Sample Pretreatment)

To 50 mg of alkyl ether carboxylate, 1.5 mL of ion exchange water and 2 mL of diethyl ether are added, to which 35% hydrochloric acid is added until the pH of the aqueous layer is pH 2 or lower. After shaking and stirring, the upper layer is collected, to which a diazomethane-ether solution is added until the yellow color disappears. To the resulting solution, nitrogen gas is charged, and after tentatively removing diazomethane, the solution is diluted with diethyl ether and subjected to GC analysis.

It is to be noted that the diazomethane-ether solution is prepared by the following procedure. Into a 300 mL distillation flask having a dropping funnel fitted with a Teflon® cock and a downward condenser, a solution of 24 g of potassium hydroxide in 52 g of water is added, to which 162 mL of carbitol and 48 mL of ether are added. The condenser is cooled with tap water. Two receivers connected in tandem are cooled with dry ice-methanol. Into the second of the two receivers, 30 mL of ether are added, and the tip of the gas introduction tube is submerged under the liquid level of ether. This flask is warmed at 70° C. in a water bath, and as ether starts to distill, a solution of 100 g of p-toluenesulfonyl-N-methyl-N-nitrosoamide dissolved in 450 mL of ether is added from the dropping funnel over approximately four hours, and the fraction thus obtained is used.

(2) Analytical Method 2;

(GC Analytical Conditions)

GC instrument: the product of Agilent Technologies, 7890A

Column: the product of Agilent Technologies, DB-5 (30 m, an inner diameter of 0.25 mm, a film thickness of 0.25 μm)

Detector: FID

Carrier: helium gas, 1 mL/min

Conditions of temperature rising: temperature is raised at a rate of 5° C./min from 100° C. to 325° C., and thereafter, maintained at 325° C. for 35 minutes.

(Method of Sample Pretreatment)

Into 50 mL of methanol, 150 mg of alkyl ether carboxylate are dissolved. Also, the cleansing composition is taken in an amount of 150 mg in terms of alkyl ether carboxylate equivalent and dissolved in 50 mL of methanol. Also, when the cleansing composition contains a strong anionic surfactant such as polyoxyethylene alkyl ether sulfate, the cleansing composition is collected in such an amount that the strong anionic surfactant is 250 mg or less. From these solutions, 1 mL is taken and applied to a solid phase cartridge (manufactured by Biotage Japan Ltd., Isolute SAX, 1 g, 3 mL, 500-0100-B) which has been conditioned with 4 mL of methanol in advance, and the filtrate is received in a 10 mL round-bottom test tube. Subsequently, the filtrate is eluted with 6 mL of a solution of 4.6 g of formic acid in 100 mL of methanol, and the eluate is also collected in the same test tube. The solution thus collected is set in a block heater heated to 50° C., to which nitrogen gas is charged, and the solution is concentrated to approximately 1 mL, and dried at room temperature by further charging nitrogen gas. To the resulting product, 2 mL of a diazomethane-ether solution is added, and the resulting solution is left to stand at room temperature for 10 minutes while stirring to carry out derivatization (methylation reaction of the alkyl ether carboxylic acid of the formula (1) by diazomethane). Subsequently, nitrogen gas is charged at room temperature and the solution is concentrated to 500 μL or less, to which chloroform is added to bring the total volume to 500 and the resulting product is subjected to GC analysis.

It is to be noted that the diazomethane-ether solution is prepared by the following procedure using a diazomethane generator (manufactured by Miyamoto Riken Ind. Co., Ltd., GM-50). A first receiver and a second receiver, and the second receiver and a third receiver are connected using a silicone rubber plug and a Teflon® tube. 0.8 g of N-methyl-N'-nitro-N-nitrosoguanidine are provided in the second receiver, to which 2.5 mL of ion exchange water are added. 10 mL of tert-butyl methyl ether are provided in the third receiver. The first, second, and third receivers are cooled on ice. Subsequently, the second receiver is fitted with a plastic syringe, into which 3 mL of a solution of 20 g of sodium hydroxide dissolved in 100 mL of ion exchange water are added. This aqueous solution of sodium hydroxide is slowly added dropwise to generate diazomethane gas, and nitrogen gas is gently charged from the first receiver side to dissolve the diazomethane gas in tert-butyl methyl ether in the third receiver, whereby a diazomethane-ether solution is obtained.

The following reagents were used in the aforementioned sample pretreatment.

Methanol (manufactured by Kanto Chemical Co., Inc., for high performance liquid chromatography, 25183-1B)

Formic acid (manufactured by Wako Pure Chemical Industries, Ltd., special grade chemical, 066-00461)

Chloroform (manufactured by Kanto Chemical Co., Inc., CICA first grade, 07278-01)

N-Methyl-N'-nitro-N-nitrosoguanidine (manufactured by Kanto Chemical Co., Inc., CICA first class, 25596-51)

Methyl tert-butyl ether (manufactured by Kanto Chemical Co., Inc., CICA special grade, 04418-00)

Sodium hydroxide (manufactured by Wako Pure Chemical Industries, Ltd., special grade, 196-13761).

EXAMPLES

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

Production Example 1

Into a stainless steel autoclave with stirring and temperature controlling functions, 1144 g (6.14 mol) of lauryl alcohol [trade name: KALCOL 2098, manufactured by Kao Corporation], 60.2 g (0.281 mol) of myristyl alcohol [trade name: KALCOL 4098, manufactured by Kao Corporation], and 2.68 g (0.0478 mol) of potassium hydroxide were added and dehydration was performed under reduced pressure. Subsequently, 996 g (22.6 mol) of ethylene oxide (EO) was introduced at 155° C. and reactions were allowed to proceed at a reaction temperature of 155° C. and a reaction pressure of 0.4 MPa for two hours. Upon completion of the reaction, the resulting mixture was stirred for 30 minutes at 80° C. under a reduced pressure condition of 6 kPa. Then, after removing unreacted ethylene oxide, nitrogen was introduced to normalize the pressure, and 4.82 g (0.0482 mol) of 90% lactic acid were added into the autoclave, followed by stirring at 80° C. for 30 minutes, whereby alkyl ethoxylate having 3.55 moles of EO added (hereinbelow, also referred to as "the produced AE") was obtained.

Into a glass reaction container with stirring and temperature controlling functions and an oxygen gas introduction tube, 90 g (0.2 mol) of the aforementioned product, 16.7 g of a 48% aqueous solution of sodium hydroxide (0.2 mol as sodium hydroxide), 0.9 g of a palladium-platinum-bismuth-based catalyst (activated carbon containing 4% of palladium, 1% of platinum, 5% of bismuth, and 50% of water), and 494.4 g of water were each added. While stirring, the liquid temperature was raised to 70° C., and while charging oxygen at a ratio of 27 mol % (with respect to the produced AE/hour), catalytic oxidation reactions were carried out at a reaction temperature of 70° C. for 3.5 hours. The rate of reaction was 89%.

Upon completion of the reaction, the catalyst was filtered out from the reaction solution to give an aqueous solution of sodium salt of alkyl ether carboxylic acid. Subsequently, 35% hydrochloric acid was added, and a liquid separation operation was performed to give alkyl ether carboxylic acid, which will be referred to as EC1.

As a result of gas chromatography analysis by Analytical Method 1 described above, it was found that, EC1 included a mixture of compounds according to formula (1), in which $M=H$, $R^1$ included lauryl group/myristyl group at a ratio of 95/5, an average carbon number was 12.1, and an average value of n was 2.8. EC1 included a component in which $n=0$ in an amount of 16% by weight, a component in which $n=1$ and a component in which $n=2$ in a total amount of 37% by weight, and components in which $n \leq 6$ in a total amount of 14% by weight.

Further, it was also found that a ratio of components having different numbers of moles of EU added in EC1, as calculated from the measurement value of the maximum component of the composition of $R^1$, was as follows: (the weight of a component in which $n=0$):(the weight of a component in which $n=1$):(the weight of a component in which $n=2$):(the weight of a component in which $n=3$):(the weight of a component in which $n=4$)=1:1.20:1.17:0.94:0.69.

As a result of gas chromatography analysis by Analytical Method 2 described above, it was found that EC1 included a mixture of compounds according to formula (1), in which, $M=H$, $R^1$ included lauryl group/myristyl group at a ratio of 95/5, an average carbon number was 12.1, and an average value of n was 2.8. EC1 included a component in which $n=0$ in an amount of 14.7% by weight, a component in which $n=1$ and a component in which $n=2$ in a total amount of 36.1% by weight, and components in which $n \leq 6$ in a total amount of 12.5% by weight.

Further, it was also found that a ratio of components having different numbers of moles of EO added in EC1, as calculated from the measurement value of the maximum component of the composition of $R^1$, was as follows: (the weight of a component in which $n=0$):(the weight of a component in which $n=1$):(the weight of a component in which $n=2$):(the weight of a component in which $n=3$):(the weight of a component in which $n=4$)=1:1.22:1.23:1.06:0.83.

Production Example 2

According to Production Example 1, EO was reacted with a raw material containing a mixture of decyl alcohol [trade name: KALCOL 1098, manufactured by Kao Corporation], lauryl alcohol [trade name: KALCOL 2098, manufactured by Kao Corporation], myristyl alcohol [trade name: KALCOL 4098, manufactured by Kao Corporation], and cetyl alcohol [trade name: KALCOL 6098, manufactured by Kao Corporation] at a weight ratio of 10/70/15/5 to give alkyl ethoxylate having 3.55 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained, which will be referred to as EC2.

As a result of gas chromatography analysis by Analytical Method 1, it was found that EC2 included a mixture of compounds according to formula (1), in which $M=H$, $R^1$ had decyl group/lauryl group/myristyl group/palmityl group at a ratio of 10/70/15/5, an average carbon number was 12.3, and an average value of n was 3.1. EC2 included a component in which $n=0$ in an amount of 16% by weight, a component in which $n=1$ and a component in which $n=2$ in a total amount of 33% by weight, and components in which $n \leq 6$ in a total amount of 18% by weight.

As a result of gas chromatography analysis by the Analytical Method 2, it was found that EC2 included a mixture of compounds according to formula (1), in which $M=H$, $R^1$ had decyl group/lauryl group/myristyl group/palmityl group at a ratio of 10/70/15/5, an average carbon number was 12.3, and an average value of n was 3.3. EC2 included a component in which $n=0$ in an amount of 15.2% by weight, a component in which $n=1$ and a component in which $n=2$ in a total amount of 31.4% by weight, and components in which $n \leq 6$ in a total amount of 21.6% by weight.

Further, it was also found that the ratio components having different numbers of moles of EO added, as calculated from the measurement value of the maximum component of the composition of $R^1$, was as follows: (the weight of a component in which $n=0$):(the weight of a component in which $n=1$):(the weight of a component in which $n=2$):(the weight of a component in which $n=3$):(the weight of a component in which $n=4$)=1:1.07:1.00:0.85:0.67.

Production Example 3

According to Production Example 1, EO was reacted with decyl alcohol as a raw material to give alkyl ethoxylate having 3.55 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis by Analytical Method 1, it was found that in the resulting mixture of compounds according to formula (1), $M=H$, $R^1$ was a decyl group, and an average value of n was 3.1. The mixture of alkyl ether carboxylic acids included a component in which $n=0$ in an amount of 16% by weight, a component in which $n=1$ and a component in which $n=2$ in a total amount of 33% by weight, and components in which $n \leq 6$ in a total amount of 18% by weight.

Production Example 4

According to Production Example 1, EO was reacted with lauryl alcohol as a raw material to give alkyl ethoxylate having 3.55 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis by Analytical Method 1, it was found that in the resulting mixture of compounds according to formula (1), $M=H$, $R^1$ was a lauryl group, and an average value of n was 3.1. The mixture of alkyl ether carboxylic acids contained a component in which $n=0$ in an amount of 16% by weight, a component in which $n=1$ and a component in which n=2 in a total amount of 33% by weight, and components in which n≤6 in a total amount of 18% by weight.

Production Example 5

According to Production Example 1, ED was reacted with myristyl alcohol as a raw material to give alkyl ethoxylate having 3.55 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis by Analytical Method 1, it was found that in the resulting mixture of compounds according to formula (1), M=H, $R^1$ was a myristyl group, and an average value of n was 3.1. The mixture of alkyl ether carboxylic acids included a component in which n=0 in an amount of 16% by weight, a component in which n=1 and a component in which n=2 in a total amount of 33% by weight, and components in which n≤6 in a total amount of 18% by weight.

Production Example 6

According to Production Example 1, EO was added to a raw material containing a mixture of lauryl alcohol and cetyl alcohol at a weight ratio of 20/80 to give alkyl ethoxylate having 3.55 moles of EU added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis by Analytical Method 1, it was found that in the resulting mixture of compounds according to formula (1), M=H, $R^1$ included lauryl group/palmityl group at a ratio of 20/80, and an average value of n was 3.1. The mixture of alkyl ether carboxylic acids included a component in which n=0 in an amount of 16% by weight, a component in which n=1 and a component in which n=2 in a total amount of 33% by weight, and components in which n≤6 in a total amount of 18% by weight.

Production Example 7

According to Production Example 1, EO was reacted with lauryl alcohol as a raw material to give alkyl ethoxylate having 3.05 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained, which will be referred to as EC23.

As a result of gas chromatography analysis by Analytical Method 1, it was found that, EC23 was a mixture of compounds according to formula (1), in which M=H, $R^1$ was a lauryl group, and an average value of n was 2.4. EC23 included a component in which n=0 in an amount of 18% by weight, a component in which n=1 and a component in which n=2 in a total amount of 43% by weight, and components in which n≤6 in a total amount of 9% by weight.

As a result of gas chromatography analysis by Analytical Method 2, it was found that, EC23 included a mixture of compounds according to formula (1), in which M=H, $R^1$ was a lauryl group, and an average value of n was 2.7. EC23 included a component in which n=0 in an amount of 17.4% by weight, a component in which n=1 and a component in which n=2 in a total amount of 37.8% by weight, and components in which n≤6 in a total amount of 13.7% by weight.

Further, it was also found that the ratio of components having different numbers of moles of EO added in EC23, as calculated from the measurement value of the maximum component of the composition of $R^1$, was as follows: (the weight of a component in which n=0):(the weight of a component in which n=1):(the weight of a component in which n=2):(the weight of a component in which n=3):(the weight of a component in which n=4)=1:1.14:1.02:0.79:0.58.

Production Example 8

According to Production Example 1, EO was reacted with lauryl alcohol as a raw material to give alkyl ethoxylate having 4.05 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained, which will be referred to as EC24.

As a result of gas chromatography analysis by Analytical Method 1, it was found that EC24 included a mixture of compounds according to formula (1), in which M=H, $R^1$ was a lauryl group, and an average value of n was 3.6. EC24 included a component in which n=0 in an amount of 11% by weight, a component in which n=1 and a component in which n=2 in a total amount of 31% by weight, and components in which n≤6 in a total amount of 24% by weight.

As a result of gas chromatography analysis by Analytical Method 2, it was found that EC24 included a mixture of compounds according to formula (1), in which M=H, $R^1$ was a lauryl group, and an average value of n was 3.5. EC24 induced a component in which n=0 in an amount of 11.4% by weight, a component in which n=1 and a component in which n=2 in a total amount of 30.6% by weight, and components in which n≤6 in a total amount of 22.2% by weight.

Further, it was also found that the ratio components having different numbers of moles of EO added, as calculated from the measurement value of the maximum component of the composition of $R^1$, was as follows: (the weight of a component in which n=0):(the weight of a component in which n=1):(the weight of a component in which n=2):(the weight of a component in which n=3):(the weight of a component in which n=4)=1:1.31:1.38:1.25:1.06.

Production Example 9

In the same manner as in Production Example 1, an alcohol-EO adduct (the produced AE) was obtained. The oxidation reaction was carried out in the same manner as in Production Example 1, except that a reaction temperature of 75° C. and a reaction time of four hours were employed. As a result, the rate of reaction was 98%. Further, the alkyl ether carboxylate thus obtained was subjected to hydrochloric acid treatment to give alkyl ether carboxylic acid, which will be referred to as EC9.

As a result of gas chromatography analysis by Analytical Method 1, it was found that EC9 included a mixture of compounds according to formula (1), in which M=H, $R^1$ had lauryl group/myristyl group at a ratio of 95/5, an average carbon number was 12.1, and an average value of n was 3.0. EC9 included a component in which n=0 in an amount of 14% by weight, a component in which n=1 and a component in which n=2 in a total amount of 34% by weight, and components in which n≤6 in a total amount of 17% by weight.

Also, the composition ratio of components in which $R^1$ was a lauryl group was found as follows: (the weight of a component in which n=0):(the weight of a component in which n=1):(the weight of a component in which n=2):(the weight of a component in which n=3):(the weight of a component in which n=4)=1:1.21:1.24:1.04:0.83.

Production Example 10

Into a stainless steel autoclave with stirring and temperature controlling functions, 1144 g (6.14 mol) of lauryl alcohol [trade name: KALCOL 2098, manufactured by Kao Corporation], 60.2 g (0.281 mol) of myristyl alcohol [trade name: KALCOL 4098, manufactured by Kao Corporation], and 2.6 g (0.0478 mol) of potassium hydroxide were added and dehydration was performed under reduced pressure. Subsequently, 718 g (16.3 mol) of ethylene oxide (EO) was introduced at 155° C. and reaction was allowed to proceed at a reaction temperature of 155° C. and a reaction pressure of 0.4 MPa for two hours. Upon completion of the reaction, the resulting mixture was cooled and then stirred for 30 minutes at 80° C. under a reduced pressure condition of 6 kPa. Then, after removing unreacted ethylene oxide, nitrogen was introduced to normalize the pressure, and 4.82 g (0.0482 mol) of 90% lactic acid were added into the autoclave, followed by stirring at 80° C. for 30 minutes, whereby alkyl ethoxylate having 2.55 moles of EO added was obtained.

Into a glass reaction container with stirring and temperature controlling functions, 600 g (2.00 mol) of the aforementioned product were added, and while stirring, the liquid temperature was raised to 70° C. Then, while adding 256 g (2.20 mol) of sodium monochloroacetate and 88 g (2.20 mol) of sodium hydroxide in divided portions, reaction was allowed to proceed for five hours. Upon completion of the reaction, 35% hydrochloric acid was added for acidification to a pH of 2.8, and the resulting oil layer was collected to obtain alkyl ether carboxylic acid, which will be referred to as EC11.

As a result of gas chromatography analysis by Analytical Method 1, it was found that EC11 included a mixture of compounds according to formula (1), in which M=H, $R^1$ included lauryl group/myristyl group at a ratio of 94/6, an average carbon number was 12.1, and an average value of n was 2.9. EC11 included a component in which n=0 in an amount of 11% by weight, a component in which n=1 and a component in which n=2 in a total amount of 37% by weight, and components in which n≤6 in a total amount of 12% by weight.

As a result of gas chromatography analysis by Analytical Method 2, it was found that, EC11 included a mixture of compounds according to formula (1), in which M=H, $R^1$ included lauryl group/myristyl group at a ratio of 94/6, an average carbon number was 12.1, and an average value of n was 3.1. EC11 included a component in which n=0 in an amount of 9.9% by weight, a component in which n=1 and a component in which n=2 in a total amount of 35.4% by weight, and components in which n≤6 in a total amount of 15.1% by weight.

Further, it was also found that the ratio of components having different numbers of moles of EO added, as calculated from the measurement value of the maximum component of the composition of $R^1$, was as follows: (the weight of a component in which n=0):(the weight of a component in which n=1):(the weight of a component in which n 2):(the weight of a component in which n=3):(the weight of a component in which n=4)=1:1.65:1.92:1.74:1.32.

Production Example 11

Into a stainless steel autoclave with stirring and temperature controlling functions, 1196 g (6.42 mol) of lauryl alcohol [trade name: KALCOL 2098, manufactured by Kao Corporation] and 2.6 g (0.0478 mol) of potassium hydroxide were added and dehydration was performed under reduced pressure. Subsequently, 846 g (19.2 mol) of ethylene oxide (EO) were introduced at 155° C. and reaction was allowed to proceed at a reaction temperature of 155° C. and a reaction pressure of 0.4 MPa for two hours. Upon completion of the reaction, the resulting mixture was cooled and stirred for 30 minutes at 80° C. under a reduced pressure condition of 6 kPa. Then, after removing unreacted ethylene oxide, nitrogen was introduced to normalize the pressure, and 4.82 g (0.0482 mol) of 90% lactic acid were added into the autoclave, followed by stirring at 80° C. for 30 minutes, whereby alkyl ethoxylate having 3.00 moles of EO added (the produced AE) was obtained.

Into a glass reaction container with stirring and temperature controlling functions, 637 g (2.00 mol) of the aforementioned product were added, and while stirring, the liquid temperature was raised to 70° C. While adding 256 g (2.20 mol) of sodium monochloroacetate and 88 g (2.20 mol) of sodium hydroxide in divided portions, reaction was allowed to proceed for five hours. Upon completion of the reaction, 35% hydrochloric acid was added for acidification until pH was 2.8, and the resulting oil layer was collected to obtain alkyl ether carboxylic acid, which will be referred to as EC27.

As a result of gas chromatography analysis by Analytical Method 2, it was found that EC27 included a mixture of compounds according to formula (1), in which M=H, $R^1$ was a lauryl group, an average carbon number was 12.0, and an average value of n was 3.5. EC27 included a component in which n=0 in an amount of 10.9% by weight, a component in which n=1 and a component in which n=2 in a total amount of 31.2% by weight, and components in which n≤6 in a total amount of 22.9% by weight.

Further, it was also found that a ratio of components having different numbers of moles of EO added, as calculated from the measurement value of the maximum component of the composition of R1, was as follows: (the weight of a component in which n=0):(the weight of a component in which n=1):(the weight of a component in which n=2):(the weight of a component in which n=3):(the weight of a component in which n=4)=1:1.45:1.41:1.29:1.07.

EC3 was obtained by mixing each of the alkyl ether carboxylic acids produced in Production Examples 3, 4, 5, and 6 at a weight ratio of 10/67.5/10/12.5.

EC4 was obtained by mixing each of the alkyl ether carboxylic acids produced in Production Examples 4, 5, and 6 at a weight ratio of 78.75/15/6.25.

EC5 was obtained by mixing EC1 obtained in Production Example 1 and the alkyl ether carboxylic acid obtained in Production Example 3 at a weight ratio of 60/40.

EC6 was obtained by mixing EC1 obtained in Production Example 1 and the alkyl ether carboxylic acid obtained in Production Example 3 at a weight ratio of 40/60.

EC7 was obtained by mixing EC2 obtained in Production Example 2 and EC24 obtained in Production Example 8 at a weight ratio of 40/60.

EC8 was obtained by mixing EC1 obtained in Production Example 1 and the alkyl ether carboxylic acid obtained in Production Example 3 at a weight ratio of 50/50.

EC26 was obtained by mixing EC1 obtained in Production Example 1 and the alkyl ether carboxylic acid obtained in Production Example 3 at a weight ratio of 30/70.

EC12 was obtained by mixing EC11 obtained in Production Example 10 and EC27 obtained in Production Example 11 at a weight ratio of 50/50.

EC13 was obtained by mixing EC11 obtained in Production Example 10 and EC22 (AKYPO RLM 45: manufactured by Kao Corporation) at a weight ratio of 50/50.

Characteristics of the mixtures as determined by Analytical Method 1 and/or Analytical Method 2 are provided in TABLE 1 and TABLE 3 below.

Examples 1 to 11 and Comparative Examples 1 to 9

Using the compounds having the compositions as shown in TABLE 1, skin cleansing agents were produced, and foaming properties, volume of foam, foam qualities, and rinsing properties were evaluated. Also, the external appearance of the skin cleansing agents at 5° C. (stability at low temperature) was visually evaluated. The results are also shown in TABLE 1.

(Production Method)

Each compound was added to ion exchange water in an amount of 15% by weight, to which a 48% aqueous solution of sodium hydroxide was added to adjust pH to 6.2, whereby a skin cleansing agent was obtained. Because Comparative Example 9 had remarkably low solubility, the skin cleansing agent was neutralized with a 48% aqueous solution of potassium hydroxide to adjust pH to 9.6. Also, the pH was measured for each skin cleansing agent diluted 20-fold with ion exchange water at 25° C.

(Evaluation Method)

One gram of each cleansing agent was placed on a hand and diluted approximately 5-fold with tap water at 30° C. The cleansing agent was lightly foamed in both hands and spread over the entire arm (from the elbow down), and foaming properties, volume of foam, and foam qualities were evaluated. Subsequently, the agent was rinsed off with tap water while rubbing both forearms with each other, and rinsing performance was evaluated based on the strength of the feeling of resistance or friction upon completion of rinsing.

Each evaluation was conducted according to the following criteria, and the results were shown as the average score of three panelists.

(1) Foaming Properties:
5: felt foaming was very quick.
4: felt foaming was quick.
3: felt foaming was normal.
2: felt foaming was slightly slow.
1: felt foaming was slow.

(2) Volume of Foam:
5: felt the volume of foam was very large.
4: felt the volume of foam was large.
3: felt the volume of foam was normal.
2: felt the volume of foam was slightly small.
1: felt the volume of foam was small.

(3) Foam Qualities (Creaminess):
5: felt finely-textured, very creamy favorable foam qualities.
4: felt creamy, favorable foam qualities.
3: felt slightly creamy foam qualities.
2: felt slightly light, coarse foam qualities.
1: felt light, coarse foam qualities.

(4) Rinsing Properties:
5: felt a very strong feeling of resistance or friction upon completion of rinsing.
4: felt a strong feeling of resistance or friction upon completion of rinsing.
3: felt a normal feeling of resistance or friction upon completion of rinsing.
2: felt a slightly weak feeling of resistance or friction upon completion of rinsing.
1: felt a weak feeling of resistance or friction upon completion of rinsing.

(5) Stability at Low Temperature:
After leaving the skin cleansing agent in storage at 5° C. for one day, the external appearance was visually observed.

TABLE 1

|  | Ex. 1 | Ex. 2 | Ex. 3 | Ex. 4 | Ex. 5 | Ex. 6 |
|---|---|---|---|---|---|---|
| Compound No. | EC1 | EC2 | EC3 | EC4 | EC5 | EC6 |
|  | Formula (1) | Formula (1) | Formula (1) | Formula (1) | Formula (1) | Formula (1) |
| R1: C10 | 0 | 10 | 10 | 0 | 40 | 60 |
| C12 | 95 | 70 | 70 | 80 | 57 | 38 |
| C14 | 5 | 15 | 10 | 15 | 3 | 2 |
| C16 | 0 | 5 | 10 | 5 | 0 | 0 |
| Analytical method 1: |  |  |  |  |  |  |
| Average carbon number | 12.1 | 12.3 | 12.4 | 12.5 | 11.3 | 10.8 |
| Average number of moles of EO added (average n) | 2.8 | 3.1 | 3.1 | 3.1 | 2.8 | 3.1 |
| Content ratio of n = 0 | 16% | 16% | 16% | 16% | 16% | 16% |
| Total amount of n = 1, 2 | 37% | 33% | 33% | 33% | 37% | 33% |
| Total amount of n ≥ 6 | 14% | 18% | 18% | 18% | 18% | 18% |
| Analytical method 2: |  |  |  |  |  |  |
| Average carbon number | 12.1 | 12.3 | — | — | 11.3 | 10.8 |
| Average number of moles of EO added (average n) | 2.8 | 3.3 | — | — | 3.0 | 3.2 |
| Content ratio of n = 0 | 14.7% | 15.2% | — | — | 13.5% | 12.5% |
| Total amount of n = 1, 2 | 36.1% | 31.4% | — | — | 34.1% | 34.8% |

TABLE 1-continued

| | | | | | | |
|---|---|---|---|---|---|---|
| Total amount of n ≥ 6 | 12.5% | 21.6% | — | — | 15.9% | 19.4% |
| M (Salt) | Na | Na | Na | Na | Na | Na |
| pH | 6.2 | 6.2 | 6.2 | 6.2 | 6.2 | 6.2 |
| External appearance | Colorless and transparent | Slightly cloudy | Colorless and transparent | Colorless and transparent | Colorless and transparent | Colorless and transparent |
| Foaming properties | 4.7 | 4.7 | 4.0 | 4.3 | 4.3 | 4.3 |
| Volume of foam | 4.3 | 4.3 | 4.3 | 4.3 | 4.0 | 4.7 |
| Foam qualities | 4.0 | 3.7 | 3.7 | 3.7 | 3.0 | 3.0 |
| Rinsing properties | 3.7 | 3.3 | 3.0 | 3.0 | 3.0 | 3.3 |
| Stability at low temperature (5° C., 1 day) | Colorless and transparent with no precipitate or sediment. | Slightly cloudy with no precipitate or sediment. | Slightly cloudy with no precipitate or sediment. | Slightly cloudy with no precipitate or sediment. | Colorless and transparent with no precipitate or sediment. | Colorless and transparent with no precipitate or sediment. |

| | Ex. 7 | Ex. 8 | Ex. 9 | Ex. 10 | Ex. 11 |
|---|---|---|---|---|---|
| Compound No. | EC7 | EC8 | EC11 | EC12 | EC13 |
| | Formula (1) | Formula (1) | Formula (1) | Formula (1) | Formula (1) |
| R1: C10 | 4 | 50 | 0 | 0 | 0 |
| C12 | 88 | 48 | 94 | 96 | 81 |
| C14 | 6 | 2 | 6 | 4 | 16 |
| C16 | 2 | 0 | 0 | 0 | 3 |
| Analytical method 1: | | | | | |
| Average carbon number | 12.1 | 11.1 | 12.1 | — | — |
| Average number of moles of EO added (average n) | 3.4 | 3.1 | 2.9 | — | — |
| Content ratio of n = 0 | 13% | 16% | 11% | — | — |
| Total amount of n = 1, 2 | 31% | 33% | 37% | — | — |
| Total amount of n ≥ 6 | 22% | 18% | 12% | — | — |
| Analytical method 2: | | | | | |
| Average carbon number | 12.1 | 11.1 | 12.1 | 12.1 | 12.4 |
| Average number of moles of EO added (average n) | 3.4 | 3.2 | 3.1 | 3.3 | 3.1 |
| Content ratio of n = 0 | 13.3% | 12.5% | 9.9% | 10.1% | 9.8% |
| Total amount of n = 1, 2 | 31.0% | 34.8% | 35.4% | 33.4% | 33.9% |
| Total amount of n ≥ 6 | 21.9% | 19.4% | 15.1% | 19.1% | 15.4% |
| M (Salt) | Na | Na | Na | Na | Na |
| pH | 6.2 | 6.2 | 6.2 | 6.2 | 6.2 |
| External appearance | Colorless and transparent | Colorless and transparent | Colorless and transparent | Colorless and transparent | Colorless and transparent |
| Foaming properties | 4.3 | 4.3 | 4.3 | 4.0 | 4.0 |
| Volume of foam | 4.3 | 4.0 | 4.0 | 4.0 | 3.7 |
| Foam qualities | 3.7 | 3.0 | 3.7 | 3.7 | 4.0 |
| Rinsing properties | 3.0 | 3.0 | 3.0 | 3.0 | 3.0 |
| Stability at low temperature (5° C., 1 day) | Colorless and transparent with no precipitate or sediment. | Colorless and transparent with no precipitate or sediment. | Colorless and transparent with no precipitate or sediment. | Colorless and transparent with no precipitate or sediment. | Colorless and transparent with no precipitate or sediment. |

| | Comp. Ex. 1 | Comp. Ex. 2 | Comp. Ex. 3 | Comp. Ex. 4 | Comp. Ex. 5 |
|---|---|---|---|---|---|
| Compound No. | EC21 *1 | EC22 *2 | EC23 | EC24 | EC25 *3 |
| | Formula (1) | Formula (1) | Formula (1) | Formula (1) | Formula (1) |
| R1: C10 | 0 | 0 | 0 | 0 | 0 |
| C12 | 68 | 68 | 100 | 100 | 100 |
| C14 | 26 | 26 | 0 | 0 | 0 |
| C16 | 6 | 6 | 0 | 0 | 0 |
| Analytical method 1: | | | | | |
| Average carbon number | 12.8 | 12.8 | 12.0 | 12.0 | 12.0 |
| Average number of moles of EO added (average n) | 3.1 | 4.6 | 2.4 | 3.6 | 3.2 |
| Content ratio of n = 0 | 16% | 7% | 18% | 11% | 3% |
| Total amount of n = 1, 2 | 33% | 20% | 43% | 31% | 38% |
| Total amount of n ≥ 6 | 18% | 39% | 9% | 24% | 13% |

TABLE 1-continued

| Analytical method 2: | | | | | |
|---|---|---|---|---|---|
| Average carbon number | — | 12.8 | 12.0 | 12.0 | 12.0 |
| Average number of moles of EO added (average n) | — | 3.2 | 2.7 | 3.5 | 2.9 |
| Content ratio of n = 0 | — | 9.6% | 17.4% | 11.4% | 2.8% |
| Total amount of n = 1, 2 | — | 31.2% | 37.8% | 30.6% | 42.8% |
| Total amount of n ≥ 6 | — | 16.1% | 13.7% | 22.2% | 6.3% |
| M (Salt) | Na | Na | Na | Na | Na |
| pH | 6.2 | 6.2 | 6.2 | 6.2 | 6.2 |
| External appearance | Cloudy | Colorless and transparent | Cloudy | Colorless and transparent | Colorless and transparent |
| Foaming properties | 2.3 | 1.3 | 5.0 | 2.0 | 3.3 |
| Volume of foam | 1.7 | 1.0 | 3.3 | 2.7 | 2.3 |
| Foam qualities | 2.3 | 2.7 | 1.7 | 2.7 | 1.0 |
| Rinsing properties | 2.3 | 2.3 | 3.3 | 2.3 | 2.3 |
| Stability at low temperature (5° C., 1 day) | Cloudy with sediment. | Colorless and transparent with no precipitate or sediment. | Cloudy with sediment. | Colorless and transparent with no precipitate or sediment. | Colorless and transparent with no precipitate or sediment. |

| | Comp. Ex. 6 | Comp. Ex. 7 | Comp. Ex. 8 | Comp. Ex. 9 |
|---|---|---|---|---|
| Compound No. | EC26 Formula (1) | EC27 Formula (1) | ES1 *4 Alkyl ether sulfate | FA1 *5 Potassium salt of mixed fatty acids |
| R1: C10 | 70 | 0 | 0 | 0 |
| C12 | 29 | 100 | 100 | 40 |
| C14 | 2 | 0 | 0 | 45 |
| C16 | 0 | 0 | 0 | 15 |
| Analytical method 1: | | | | |
| Average carbon number | 10.6 | — | 12.0 | 13.5 |
| Average number of moles of EO added (average n) | 3.1 | — | 10 | — |
| Content ratio of n = 0 | 16% | — | — | — |
| Total amount of n = 1, 2 | 33% | — | — | — |
| Total amount of n ≥ 6 | 18% | — | — | — |
| Analytical method 2: | | | | |
| Average carbon number | 10.6 | 12.0 | — | — |
| Average number of moles of EO added (average n) | 3.2 | 3.5 | — | — |
| Content ratio of n = 0 | 12.5% | 10.9% | — | — |
| Total amount of n = 1, 2 | 34.8% | 31.2% | — | — |
| Total amount of n ≥ 6 | 19.4% | 22.9% | — | — |
| M (Salt) | Na | Na | Na | K |
| pH | 6.2 | 6.2 | 6.2 | 9.6 |
| External appearance | Colorless and transparent | Colorless and transparent | Colorless and transparent | Slightly cloudy |
| Foaming properties | 4.7 | 2.0 | 4.7 | 2.0 |
| Volume of foam | 3.0 | 2.7 | 4.0 | 5.0 |
| Foam qualities | 2.0 | 2.7 | 1.0 | 5.0 |
| Rinsing properties | 3.0 | 2.3 | 1.0 | 5.0 |
| Stability at low temperature (5° C., 1 day) | Colorless and transparent with no precipitate or sediment. | Colorless and transparent with no precipitate or sediment. | Colorless and transparent with no precipitate or sediment. | Cloudy with sediment. |

*1 AKYPO RLM25 [manufactured by Kao Corporation];
*2 AKYPO RLM45 [manufactured by Kao Corporation];
*3 BEAULIGHT LCA [manufactured by Sanyo Chemical Industries, Ltd.];
*4 EMAL 125A [manufactured by Kao Corporation];
*5 Prepared by mixing Lauric acid [LUNAC L-98, manufactured by Kao Corporation], myristic acid [LUNAC MY-98, manufactured by Kao Corporation], and palmitic acid [LUNAC P-95, manufactured by Kao Corporation] at a ratio of 40:45:15.

Examples 12 to 18 and Comparative Examples 10 to 15

In the same manner as in Examples 1 to 11, skin cleansing agents were produced so that each component shown in TABLE 3 was contained in an amount of 3% by weight, and the percentage residual sebum and feeling on the skin under conditions of high temperature and high humidity were evaluated by the method described below. The results are also shown in TABLE 3.

(Evaluation Method)
(1) Percentage Residual Sebum:

On the inside of the forearm, a circle 3.5 cm in diameter was marked, which served as a test site. The L, a, and b values are measured using a colorimeter (chroma meter CR-300, Konica Minolta) in advance to obtain the skin color of the test site $(\Delta E^*ab=[(\Delta L^*)^2+(a^*)^2+(b^*)^2]^{1/2})$. Into the model comedo sebum shown in TABLE 2, carbon black was dispersed in an amount of 2% by weight and dissolved in a warm water bath of 50° C., from which 20 μL was uniformly applied to the test site. After leaving for 15 minutes, the color was measured with the colorimeter.

TABLE 2

(Model comedo sebum composition)

| | (% by weight) |
|---|---|
| Squalene | 7.9 |
| Myristyl myristate | 13.9 |
| Cottonseed oil | 7.1 |
| Cholesterol | 11.9 |
| Cholesteryl palmitate | 4.0 |
| Lauric acid | 0.8 |
| Myristic acid | 6.3 |
| Palmitic acid | 24.6 |
| Stearic acid | 4.8 |
| Oleic acid | 18.7 |
| Total | 100.0 |

Each cleansing agent was put in a pump foamer and 0.8 g (one push) of foam was put onto the test site, followed by massaging for 20 times with the tip of the index finger. The foam was then rinsed off with 20 mL of tap water.

After five minutes, the skin color after washing was measured, and the percentage residual model sebum left on the skin was calculated by the following formula.

Percentage residual sebum (%) =

$$1 - \frac{(\text{skin color after washing}) - (\text{skin color after application of model sebum})}{(\text{original skin color}) - (\text{skin color after application of model sebum})}$$

(2) The Feeling on the Skin Under Conditions of High Temperature and High Humidity.

One gram of each cleansing agent was placed on a hand and diluted approximately 5-fold with tap water of 30° C. The cleansing agent was lightly foamed in both hands and spread over the entire arm (from the elbow down) to wash it. Subsequently, the foam was rinsed off with tap water and lightly wiped with a towel. Subsequently, the tester moved to an environment variable room where the room temperature was set at 40° C. and the relative humidity was set at 75%, and evaluated the feeling on the skin 30 seconds after entering the room, and the skin feel under conditions of high temperature and high humidity was scored according to the following criteria. This test was conducted by one expert panelist.

5: Felt no stickiness of the skin but a very strong smooth feeling.
4: Felt no stickiness of the skin but a strong smooth feeling.
3: Felt a moderate smooth feeling of the skin.
2: Strongly felt a sticky feeling, feeling of friction, or slimy feeling of the skin.
1: Very strongly felt a sticky feeling, feeling of friction, or slimy feeling of the skin.

TABLE 3

| | Example 12 | Example 13 | Example 14 | Example 15 | Example 16 | Example 17 | Example 18 |
|---|---|---|---|---|---|---|---|
| Compound No. | EC1 | EC2 | EC3 | EC4 | EC6 | EC7 | EC11 |
| | Formula (1) | Formula (1) | Formula (1) | Formula (1) | Formula (1) | Formula (1) | Formula (1) |
| R1: C10 | 0 | 10 | 10 | 0 | 60 | 4 | 0 |
| C12 | 95 | 70 | 70 | 80 | 38 | 88 | 95 |
| C14 | 5 | 15 | 10 | 15 | 2 | 6 | 5 |
| C16 | 0 | 5 | 10 | 5 | 0 | 2 | 0 |
| Analytical method 1: | | | | | | | |
| Average carbon number | 12.1 | 12.3 | 12.4 | 12.5 | 10.8 | 12.1 | 12.1 |
| Average number of moles of EO added (average n) | 2.8 | 3.1 | 3.1 | 3.1 | 3.1 | 3.4 | 2.9 |
| Content ratio of n = 0 | 16% | 16% | 16% | 16% | 16% | 13% | 11% |
| Total amount of n = 1, 2 | 37% | 33% | 33% | 33% | 33% | 31% | 37% |
| Total amount of n ≥ 6 | 14% | 18% | 18% | 18% | 18% | 22% | 12% |
| Analytical method 2: | | | | | | | |
| Average carbon number | 12.1 | 12.3 | — | — | 10.8 | 12.1 | 12.1 |
| Average number of moles of EO added (average n) | 2.8 | 3.3 | — | — | 3.2 | 3.4 | 3.1 |
| Content ratio of n = 0 | 14.7% | 15.2% | — | — | 12.5% | 13.3% | 9.9% |
| Total amount of n = 1, 2 | 36.1% | 31.4% | — | — | 34.8% | 31.0% | 35.4% |
| Total amount of n ≥ 6 | 12.5% | 21.6% | — | — | 19.4% | 21.9% | 15.1% |
| M (Salt) | Na | Na | Na | Na | Na | Na | Na |
| pH | 6.2 | 6.2 | 6.2 | 6.2 | 6.2 | 6.2 | 6.2 |
| Percentage residual sebum (%) | 4.3 | 8.4 | 10.1 | 11.6 | 9.8 | 11.1 | 7.4 |
| Feeling on the skin | 4 | 4 | 4 | 4 | 4 | 4 | 4 |

| | Comparative Example 10 | Comparative Example 11 | Comparative Example 12 | Comparative Example 13 | Comparative Example 14 | Comparative Example 15 |
|---|---|---|---|---|---|---|
| Compound No. | EC21 *1 | EC22 *2 | EC24 | EC25 *3 | ES1 *4 | FA1 *5 |
| | Formula (1) | Formula (1) | Formula (1) | Formula (1) | Alkyl ether sulfate | Potassium salt of mixed fatty acids |
| R1: C10 | 0 | 0 | 0 | 0 | 0 | 0 |
| C12 | 68 | 68 | 100 | 100 | 100 | 40 |
| C14 | 26 | 26 | 0 | 0 | 0 | 45 |
| C16 | 6 | 6 | 0 | 0 | 0 | 15 |

TABLE 3-continued

Analytical method 1:

| | | | | | | |
|---|---|---|---|---|---|---|
| Average carbon number | 12.8 | 12.8 | 12.0 | 12.0 | 12.0 | 13.5 |
| Average number of moles of EO added (average n) | 3.1 | 4.6 | 3.6 | 3.2 | 1.0 | — |
| Content ratio of n = 0 | 16% | 7% | 11% | 3% | — | — |
| Total amount of n = 1, 2 | 33% | 20% | 31% | 38% | — | — |
| Total amount of n ≥ 6 | 18% | 39% | 24% | 13% | — | — |

Analytical method 2:

| | | | | | | |
|---|---|---|---|---|---|---|
| Average carbon number | 12.8 | 12.8 | 12.0 | 12.0 | 12.0 | 13.5 |
| Average number of moles of EO added (average n) | 2.0 | 3.2 | 3.5 | 2.9 | 1.0 | — |
| Content ratio of n = 0 | 23.7% | 9.6% | 11.4% | 2.8% | — | — |
| Total amount of n = 1, 2 | 41.5% | 31.2% | 30.6% | 42.8% | — | — |
| Total amount of n ≥ 6 | 5.6% | 16.1% | 22.2% | 6.3% | — | — |
| M (Salt) | Na | Na | Na | Na | Na | K |
| pH | 6.2 | 6.2 | 6.2 | 6.2 | 6.2 | 9.6 |
| Percentage residual sebum (%) | 18.3 | 19.1 | 21.6 | 20.4 | 28.7 | 28.4 |
| Feeling on the skin | 3 | 3 | 3 | 2 | 1 | 1 |

*1 AKYPO RLM25 [manufactured by Kao Corporation];
*2 AKYPO RLM45 [manufactured by Kao Corporation];
*3 BEAULIGHT LCA [manufactured by Sanyo Chemical Industries, Ltd.];
*4 EMAL 125A [manufactured by Kao Corporation];
*5 Prepared by mixing Lauric acid [LUNAC L-98, manufactured by Kao Corporation], myristic acid [LUNAC MY-98, manufactured by Kao Corporation], and palmitic acid [LUNAC P-95, manufactured by Kao Corporation] at a ratio of 40:45:15.

Comparative evaluation of Examples 19 and 20 and Comparative Example 16 (commercially available soap formulation product).

Body cleansing agents having the compositions as shown in TABLE 4 were produced by the following method and the alleviating effects of daily use of these agents on pimples on the back were evaluated by the following method. The commercially available soap formulation product used as Comparative Example 16 was Dove•Beauty Moisture Body Wash (manufactured by Unilever Japan K.K.), which contains water, myristic acid, lauric acid, potassium hydroxide, palmitic acid, sodium lauryl sulfate, glycerin, glycol distearate, cocamidopropyl betaine, PG, hydroxypropyl methylcellulose, guar hydroxypropyltrimonium chloride, etidronic acid, BHT, EDTA-47Na, methylisothiazolinone, and fragrances. It should be noted that Example 19 had a formulation which was adjusted so as to give approximately the same volume of foam upon application as the commercially available soap formulation product of Comparative Example 16, which was used for comparison.

TABLE 4

| Component (% by weight) | Example 19 | Example 20 |
|---|---|---|
| Compound EC1 | 20 | |
| Compound EC11 | | 20 |
| POE alkyl ether sulfate *6 | 1 | 1 |
| Alkyl (C8-16) glucoside *7 | 4 | 4 |
| Lauryl amidopropyl betaine *8 | 2.7 | 2.7 |
| Propylene glycol | 1 | 1 |
| Glycol distearate | 2 | 2 |
| Aqueous solution of sodium hydroxide | q.s. | q.s. |
| Fragrance | Trace | Trace |
| Purified water | Balance | Balance |
| Total | 100 | 100 |
| pH | 6.2 | 6.2 |

*6 containing 3.7% of EMAL 227 [manufactured by Kao Corporation, POE alkyl ether sulfate, 27% aqueous solution].
*7 containing 10% of AG-124 [manufactured by Kao Corporation, alkyl (C8-C16) glucoside, 40% aqueous solution].
*8 containing 9% of AMPHITOL 20 AB [manufactured by Kao Corporation, lauryl amidopropyl betaine, 30% aqueous solution].

(Production Method)

Each component except for fragrances was added and dissolved in purified water heated to 80° C. while stirring. Subsequently, the resulting mixture was cooled to 40° C., to which fragrances were added. The mixture was then homogenized and cooled to room temperature to give a body cleansing agent.

(Evaluation Method)

Five grams of the cleansing agent of Comparative Example 16 were placed on a hand of a subject having pimples on the back, and while foaming the agent with warm water, the subject washed the whole body by palm and then rinsed the foam off with a shower at 40° C. The subject washed the body in this manner daily once at night. Three weeks later, the back was photographed (no change was observed).

From the next day, the subject washed the body using the cleansing agent of Example 19 similarly for three weeks, and then the back was similarly photographed (Photograph 1).

Further, from the next day, the subject washed the body using the cleansing agent of Comparative Example 16 similarly for three weeks, and then the back was similarly photographed (Photograph 2).

The photographs taken are shown in FIG. 1.

From the results of FIG. 1, continuous use of the body cleansing agent of Example 19 considerably reduced pimples on the back, and also redness was reduced. In contrast, when the use of the body cleansing agent of Example 19 was discontinued and replaced by the body cleansing agent of Comparative Example 16, pimples on the back increased and patchy redness appeared on the skin. The body cleansing agent of Example 19, which is a body cleansing agent according to the present invention exhibited a high skin-cleansing property in an actual cleansing experiment, showing a high effect of removing comedo sebum, which is considered to cause pimples. Thus, from these results, exemplary cleansing agents according to the present invention are considered to lead to suppression of pimples. A similar result was obtained with the use of the body cleansing agent of Example 20.

Examples 21 to 24

Skin cleansing agents having the compositions shown in TABLE 5 were produced by a routine method, and foaming performance, rinsing properties, and feeling on the skin were evaluated. All of the compositions exhibited favorable foaming properties, volume of foam, foam qualities, and rinsing properties as well as excellent sebum cleansing properties, and left no stickiness on the skin after towel drying. Further, with regard also to the feeling on the skin under conditions of high temperature and high humidity, a strong smooth feeling was felt.

TABLE 5

| Component (% by weight) | Example 21 | Example 22 | Example 23 | Example 24 |
|---|---|---|---|---|
| Compound EC1 | 7 | | | |
| Compound EC9 | | 15 | 3 | 0.5 |
| Sorbitol | 7 | 7 | 7 | 5 |
| Aqueous solution of potassium hydroxide | q.s. | q.s. | q.s. | q.s. |
| Fragrance | Trace | Trace | Trace | Trace |
| Purified water | Balance | Balance | Balance | Balance |
| Total | 100 | 100 | 100 | 100 |
| pH | 10.4 | 10.0 | 10.0 | 10.0 |

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cleansing composition, comprising:
a mixture of alkyl ether carboxylic acids and/or salts thereof, each having a structure according to formula (1):

$$R^1-O-(CH_2CH_2O)_n-CH_2-COOM \qquad (1)$$

where:
$R^1$ is an alkyl group having 4 to 22 carbon atoms;
n is a number of from 0 to 20; and
M is a hydrogen atom, alkali metal, alkaline earth metal, $NH_4^+$, or organic ammonium;
wherein:
the mixture includes alkyl ether carboxylic acids and/or salts having at least two different alkyl groups $R^1$;
an average carbon number of alkyl groups $R^1$ of alkyl ether carboxylic acids and/or salts in the mixture is from 10.8 to 12.5;
the mixture includes alkyl ether carboxylic acids and/or salts in which n=0 in an amount of from 8 to 27% by weight based on a total weight of the mixture;
the mixture includes alkyl ether carboxylic acids and/or salts in which n=1 and alkyl ether carboxylic acids and/or salts in which n=2 in a total amount of from 28 to 38% by weight based on the total weight of the mixture; and
the mixture includes alkyl ether carboxylic acids and/or salts in which n≥6 in an amount of at least 10% by weight based on the total weight of the mixture.

2. The cleansing composition according to claim 1, wherein the mixture includes alkyl ether carboxylic acids and/or salts in a weight ratio of $(W_0):(W_1):(W_2):(W_3):(W_4)$ of
(1):(0.99 to 3.50):(0.89 to 3.00):(0.76 to 3.00):(0.63 to 1.52);
wherein:
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and
$W_4$ is a total weight of alkyl ether carboxylic acids and/or salts in the mixture in which n=4.

3. The cleansing composition according to claim 1, wherein:
the mixture includes alkyl ether carboxylic acids and/or salts in which n=0 in an amount of from 8 to less than 12% by weight based on a total weight of the mixture;
the mixture includes alkyl ether carboxylic acids and/or salts in a weight ratio of $(W_0):(W_1):(W_2):(W_3):(W_4)$ of
(1):(1.53 to 1.87):(1.59 to 2.25):(1.33 to 2.16):(1.00 to 1.52);
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and
$W_4$ is a total weight of alkyl ether carboxylic acids and/or salts in the mixture in which n=4.

4. The cleansing composition according to claim 1, wherein:
the mixture includes alkyl ether carboxylic acids and/or salts in which n=0 in an amount of from 12 to 17% by weight based on a total weight of the mixture;
the mixture includes alkyl ether carboxylic acids and/or salts in a weight ratio of $(W_0):(W_1):(W_2):(W_3):(W_4)$ of
(1):(0.99 to 1.34):(0.89 to 1.40):(0.76 to 1.23):(0.63 to 0.99);
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and
$W_4$ is a total weight of alkyl ether carboxylic acids and/or salts in the mixture in which n=4.

5. The cleansing composition according to claim 1, wherein:
the mixture includes alkyl ether carboxylic acids and/or salts in which n=0 in an amount of from 8 to 11.8% by weight based on a total weight of the mixture;
the mixture includes alkyl ether carboxylic acids and/or salts in a weight ratio of $(W_0):(W_1):(W_2):(W_3):(W_4)$ of
(1):(1.58 to 1.84):(1.72 to 2.17):(1.49 to 2.00):(1.00 to 1.52);
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and $W_4$ is a total weight of alkyl ether carboxylic acids and/or salts in the mixture in which n=4.

6. The cleansing composition according to claim 1, wherein:
the mixture includes alkyl ether carboxylic acids and/or salts in which n=0 in an amount of from 13 to 17% by weight based on a total weight of the mixture;
the mixture includes alkyl ether carboxylic acids and/or salts in a weight ratio of $(W_0):(W_1):(W_2):(W_3):(W_4)$ of (1):(1.00 to 1.31):(0.93 to 1.34):(0.79 to 1.18):(0.63 to 0.99);
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and
$W_4$ is a total weight of alkyl ether carboxylic acids and/or salts in the mixture in which n=4.

7. The cleansing composition according to claim 1, wherein:
the mixture includes alkyl ether carboxylic acids and/or salts in which n=0 in an amount of from 13 to 16% by weight based on a total weight of the mixture;
the mixture includes alkyl ether carboxylic acids and/or salts in a weight ratio of $(W_0):(W_1):(W_2):(W_3):(W_4)$ of (1):(1.00 to 1.25):(1.10 to 1.30):(0.85 to 1.10):(0.65 to 0.90);
wherein:
$W_0$ is a total weight of alkyl ether carboxylic acids and/or salts in the mixture in which n=0;
$W_1$ is a total weight of alkyl ether carboxylic acids and/or salts in the mixture in which n=1;
$W_2$ is a total weight of alkyl ether carboxylic acids and/or salts in the mixture in which n=2;
$W_3$ is a total weight of alkyl ether carboxylic acids and/or salts in the mixture in which n=3; and
$W_4$ is a total weight of alkyl ether carboxylic acids and/or salts in the mixture in which n=4.

8. The cleansing composition according to claim 1, wherein the mixture includes alkyl ether carboxylic acids and/or salts having alkyl groups $R^1$ having a highest carbon number in an amount of from 55 to less than 97% by weight based on the total weight of the mixture.

9. The cleansing composition according to claim 1, wherein an average value of n of alkyl ether carboxylic acids and/or salts in the mixture is from 1.5 to 3.5.

10. The cleansing composition according to claim 1, wherein the cleansing composition is a skin cleansing composition.

11. A cleansing composition, comprising
a mixture of alkyl ether carboxylic acids and/or salts thereof, each having a structure according to formula (1):

$$R^1\text{—}O\text{—}(CH_2CH_2O)_n\text{—}CH_2\text{—}COOM \tag{1}$$

where:
$R^1$ is an alkyl group having 4 to 22 carbon atoms;
n is a number of from 0 to 20; and
M is a hydrogen atom, alkali metal, alkaline earth metal, $NH_4^\pm$, or organic ammonium;
wherein:
the mixture includes alkyl ether carboxylic acids and/or salts having at least two different alkyl groups $R^1$;
an average carbon number of alkyl groups $R^1$ of alkyl ether carboxylic acids and/or salts in the mixture is from 10.8 to 12.5;
the mixture includes alkyl ether carboxylic acids and/or salts in which n=0 in an amount of from 13 to 27% by weight based on a total weight of the mixture; and
the mixture includes alkyl ether carboxylic acids and/or salts in which n≥6 in an amount of at least 10% by weight based on the total weight of the mixture.

12. A skin cleansing method, comprising:
applying the cleansing composition according to claim 1 to an area of skin on a body;
washing the area of skin on the body; and
rinsing the area of skin on the body.

13. The cleansing composition according to claim 1, consisting essentially of the mixture of alkyl ether carboxylic acids and/or salts thereof and water.

14. The cleansing composition according to claim 1, consisting of the mixture of alkyl ether carboxylic acids and/or salts thereof, water, and optionally at least one member selected from the group consisting of surfactants other than those represented by formula (1), humectants, oil components, disinfecting agents, anti-inflammatory agents, preservatives, chelating agents, thickening agents, pearlescent agents, fragrances, cooling agents, dyes, ultraviolet absorbers, antioxidants, and plant extracts.

15. The cleansing composition according to claim 1, further comprising a polyoxyethylene alkyl ether sulfate, an alkyl glucoside, and lauryl amidopropyl betaine.

16. A cleansing composition, comprising
a mixture of alkyl ether carboxylic acids and/or salts thereof, each having a structure according to formula (1):

$$R^1\text{—}O\text{—}(CH_2CH_2O)_n\text{—}CH_2\text{—}COOM \tag{1}$$

where:
$R^1$ is an alkyl group having 4 to 22 carbon atoms;
n is a number of from 0 to 20; and
M is a hydrogen atom, alkali metal, alkaline earth metal, $NH_4^\pm$, or organic ammonium;
wherein:
the mixture includes alkyl ether carboxylic acids and/or salts having at least two different alkyl groups $R^1$;
an average carbon number of alkyl groups $R^1$ of alkyl ether carboxylic acids and/or salts in the mixture is from 10.8 to 12.5; and
an average value of n for alkyl ether carboxylic acids and/or salts in the mixture is from 1.5 to 2.8.

17. The cleansing composition of claim 16, wherein the average value of n for alkyl ether carboxylic acids and/or salts in the mixture is from 1.5 to 2.7.

18. The cleansing composition of claim 16, wherein the cleansing composition is a skin cleansing composition.

* * * * *

UNITED STATES PATENT AND TRADEMARK OFFICE
CERTIFICATE OF CORRECTION

PATENT NO. : 8,703,108 B2
APPLICATION NO. : 13/760096
DATED : April 22, 2014
INVENTOR(S) : Hiroki Takeuchi et al.

It is certified that error appears in the above-identified patent and that said Letters Patent is hereby corrected as shown below:

In the Claims

Column 29, line 45: "$NH_4^{\pm}$" should read --$NH_4^{+}$--

Column 32, line 5: "$NH_4^{\pm}$" should read --$NH_4^{+}$--

Column 32, line 45: "$NH_4^{\pm}$" should read --$NH_4^{+}$--

Signed and Sealed this
Twenty-sixth Day of August, 2014

Michelle K. Lee
*Deputy Director of the United States Patent and Trademark Office*